United States Patent
Chien et al.

(10) Patent No.: US 9,060,824 B2
(45) Date of Patent: Jun. 23, 2015

(54) BONE SCREW, METHOD FOR MANUFACTURING THE BONE SCREW, AND TOOL FOR MOUNTING AND REMOVING THE BONE SCREW

(71) Applicant: METAL INDUSTRIES RESEARCH & DEVELOPMENT CENTRE, Kaohsiung (TW)

(72) Inventors: Chi-Sheng Chien, Tainan (TW); Tsung-Chih Yu, Tainan (TW); Chung-Hsing Yu, Tainan (TW); Shien-Nan Kuo, Kaohsiung (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 158 days.

(21) Appl. No.: 13/678,772

(22) Filed: Nov. 16, 2012

(65) Prior Publication Data
US 2013/0131733 A1   May 23, 2013

(30) Foreign Application Priority Data
Nov. 17, 2011 (TW) .............................. 100141775 A

(51) Int. Cl.
*A61B 17/86* (2006.01)
*A61B 17/88* (2006.01)

(52) U.S. Cl.
CPC ....... *A61B 17/8685* (2013.01); *Y10T 29/49826* (2015.01); *A61B 17/864* (2013.01); *A61B 17/866* (2013.01); *A61B 17/8875* (2013.01)

(58) Field of Classification Search
CPC . A61B 17/8685; A61B 17/866; A61B 17/864
USPC ........................................ 606/323, 328, 316
See application file for complete search history.

(56) References Cited

U.S. PATENT DOCUMENTS

| | | | |
|---|---|---|---|
| 4,175,555 A | 11/1979 | Herbert | |
| 7,625,395 B2 | 12/2009 | Muckter | |
| 2006/0129147 A1* | 6/2006 | Biedermann et al. | 606/61 |
| 2007/0016208 A1 | 1/2007 | Thornes | |
| 2009/0062868 A1* | 3/2009 | Casutt | 606/316 |
| 2010/0076504 A1 | 3/2010 | McNamara et al. | |

* cited by examiner

*Primary Examiner* — Andrew Yang
(74) *Attorney, Agent, or Firm* — WPAT, PC; Justin King

(57) ABSTRACT

A bone screw includes a front portion, a rear portion, and a shaft portion. The shaft portion is fixedly joined to the front portion and the rear portion, so as to form an integral bone screw. The Young's modulus of the shaft portion is smaller than that of the front portion and that of the rear portion.

8 Claims, 6 Drawing Sheets

BONE SCREW, METHOD FOR MANUFACTURING THE BONE SCREW, AND TOOL FOR MOUNTING AND REMOVING THE BONE SCREW

CROSS-REFERENCE TO RELATED APPLICATION

This application claims the benefit of Taiwan Patent Application No. 100141775, filed on Nov. 17, 2011, which is hereby incorporated by reference for all purposes as if fully set forth herein.

BACKGROUND OF THE INVENTION

1. Field of Invention

The present invention relates to a method for manufacturing a bone screw, and a tool for mounting and removing the bone screw, and more particularly to a bone screw where the Young's modulus of a shaft portion is smaller than that of a front portion and that of a rear portion.

2. Related Art

The work and life style in most areas of Asia is characterized in high population density, a great many motor vehicles, intensive labor forces, and gradually aging population. In recent years, the Asian economic environment and conditions are improved. In addition, the Asian body type is different from that of the westerners, and the causes of bone trauma in Asia are different from those in Europe and America which are mainly sports injuries. Therefore, the innovation and researches for bone trauma treatment products and equipment related to bone surgeries become more and more important in Asia.

Referring to FIG. 1, U.S. Pat. No. 4,175,555 discloses a bone screw 10. The bone screw 10 includes a front portion 20, a rear portion 30, and a shaft portion 40. The shaft portion 40 is located between the front portion 20 and the rear portion 30. The front portion 20 and the rear portion 30 of the bone screw 10 each have a thread with a different pitch and diameter, and are capable of compressing and drawing together two screwed bones. However, the shaft portion, the front portion, and the rear portion of the bone screw are integrally formed and manufactured with the same metal material, which fails to provide a relative micro-motion and an external buffer force between the two bones, and may further result in joint dislocation for a second time or uncompleted bone reposition when patients do exercise after the surgeries.

Referring to FIG. 2, U.S. Pat. No. 7,625,395 discloses an implantable screw 60 for stabilization of a joint or a bone fracture. The implantable screw 60 includes a front portion 70, a rear portion 80, and a flexible shaft portion 90. The flexible shaft portion 90, located between the front portion 70 and the rear portion 80, is capable of preventing axial tension between the front portion 70 and the rear portion 80, but allows small displacement in other directions. The flexible shaft portion 90 is formed by multiple sutures, instead of a hollow cylinder structure, and is not fixedly connected to the front portion 70 and the rear portion 80. However, in the foregoing patent, as the front portion and the rear portion are merely connected by using surgical sutures, the surgery process is complicated, a large wound needs to be opened to perform an operation, and the fixation strength is undesirable.

Therefore, it is required to provide a bone screw capable of solving the foregoing problems.

SUMMARY OF THE INVENTION

The present invention provides a bone screw including a front portion, a rear portion, and a shaft portion. The shaft portion is fixedly joined to the front portion and the rear portion, so as to form an integral bone screw. The Young's modulus of the shaft portion is smaller than that of the front portion and that of the rear portion.

The bone screw of the present invention has a fixing function in the case of a bone fracture or joint dislocation, and mainly has the following advantages. 1. The Young's modulus of the shaft portion is smaller than that of the front portion and that of the rear portion, thereby providing the bone screw with moderate elasticity. 2. After being fixed into two bones of the body, the bone screw can buffer and absorb the receiving force, thereby decreasing the force received by the bones when the front and rear portions are fixed therein, and further lowering the loosening probability of the bone screw. 3. The bone screw is integrally designed, so the wound after a surgery is small; and the bone screw respectively passes through and fixedly unites a first bone and a second bone, so as to reposition and fix the dislocated/fractured portion, thereby simplifying the surgical procedures and shortening the surgery duration.

To make the above and other purposes, features, and advantages of the present invention more comprehensible, the present invention is described in detail below with reference to the accompanying drawings.

BRIEF DESCRIPTION OF THE DRAWINGS

The present invention will become more fully understood from the detailed description given herein below for illustration only, and thus are not limitative of the present invention, and wherein.

DETAILED DESCRIPTION OF THE INVENTION

Figure 1:
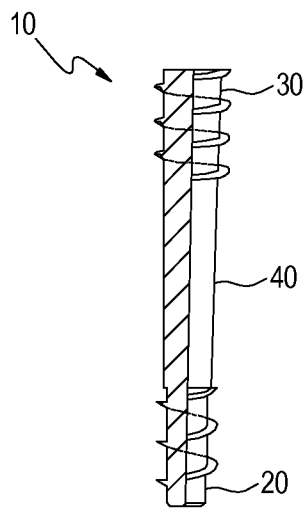
FIG. 1 is a schematic partial sectional view of a first type of bone screw in the prior art.
Figure 2:
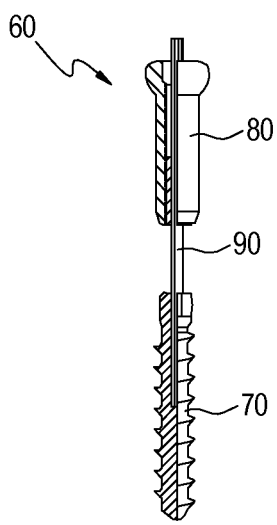
FIG. 2 is a schematic partial sectional view of a second type of bone screw in the prior art.
Figure 3:
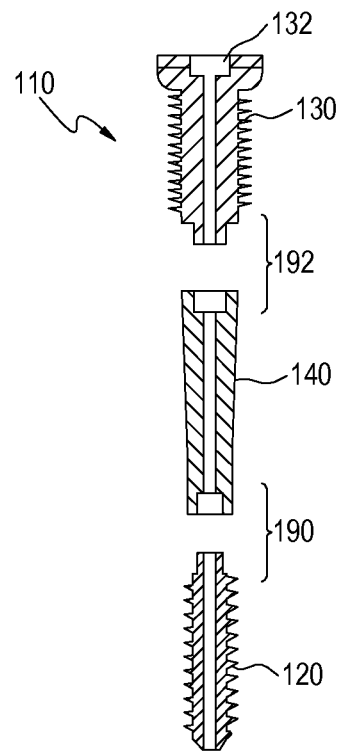
FIG. 3 is a schematic exploded sectional view of a bone screw according to a first embodiment of the present invention.
Figure 4:
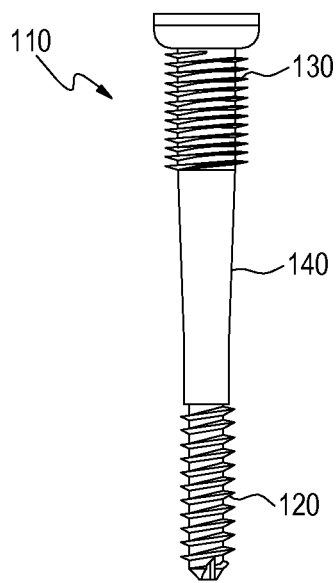
FIG. 4 is a schematic combined plan view of the bone screw according to the first embodiment of the present invention.

FIG. 3 and FIG. 4 show a method for manufacturing a bone screw according to a first embodiment of the present invention. Referring to FIG. 3, a front portion 120, a shaft portion 140, and a rear portion 130 are provided, wherein outer surfaces of the front portion 120 and the rear portion 130 are formed with threads. In this embodiment, preferably, the front portion 120, the shaft portion 140, and the rear portion 130 are all hollow inside and in communication with each other. The rear portion 130 includes a polygonal hole 132 located at a central line of the rear portion 130. The Young's Modulus of the shaft portion 140 is smaller than that of the front portion 120 and that of the rear portion 130. The front portion 120 and the rear portion 130 are fixedly joined to the shaft portion 140 through a joint structure 190 and a joint structure 192 respectively, so as to form an integral bone screw 110, as shown in FIG. 4. The joint structures 190 and 192 are used to respectively join the front portion 120 and the rear portion 130 to a leading end and a trailing end of the shaft portion 140 in a screwing manner, a snapping manner, an injection molding manner, or an adhering manner.

Figure 5:
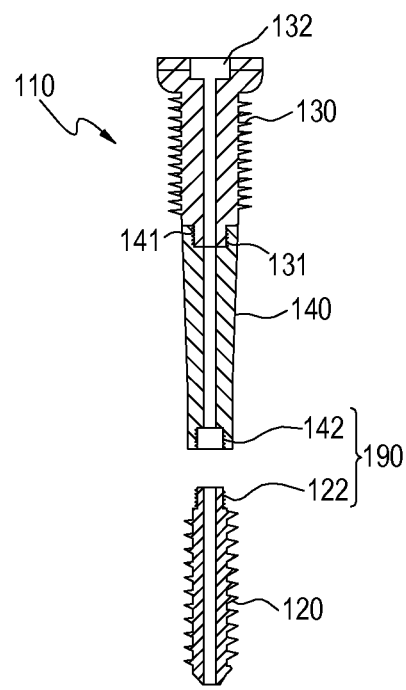
FIG. 5 is a schematic exploded sectional view of a joint structure in a first implementation manner of the present invention.

Referring to FIG. 5, it shows a joint structure 190 according to a first implementation manner of the present invention. In a screwing manner of the joint structure 190, the front portion 120 (similar to a plug) includes a first thread 122, and a leading end (similar to a socket) of the shaft portion 140 includes a first screw hole 142, that is, the first thread 122 and the first screw hole 142 are formed to the joint structure 190. When the first thread 122 of the front portion 120 is screwed into the first screw hole 142 of the shaft portion 140, the front portion 120 is joined to the leading end of the shaft portion 140. Likewise, when a second thread 131 of the rear portion 130 is screwed into a second screw hole 141 of the shaft portion 140, the rear portion 130 is joined to a trailing end of the shaft portion 140.

Figure 6:
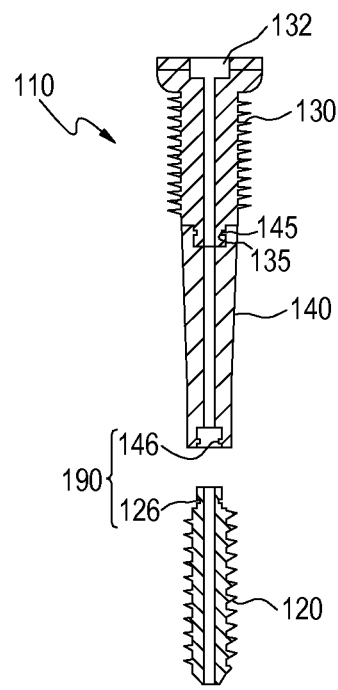
FIG. 6 is a schematic exploded sectional view of a joint structure in a second implementation manner of the present invention.

Referring to FIG. 6, it shows a joint structure 190 according to a second implementation manner of the present invention. In a snapping manner of the joint structure 190, the front portion 120 (similar to a plug) includes a first groove 126, and a leading end (similar to a socket) of the shaft portion 140 includes a first protrusion 146, that is, the first groove 126 and the first protrusion 146 are formed to the joint structure 190. When the first protrusion 146 of the shaft portion 140 is snapped into the first groove 126 of the front portion 120, the front portion 120 is joined to the leading end of the shaft portion 140. Since the Young's Modulus of the shaft portion 140 is smaller than that of the front portion 120, the protrusion of the shaft portion 140 is easily deformed and then snapped into the groove of the front portion 120. Likewise, when a second protrusion 145 of the shaft portion 140 is snapped into a second groove 135 of the rear portion 130, the rear portion 130 is joined to a trailing end of the shaft portion 140.

Figure 7:
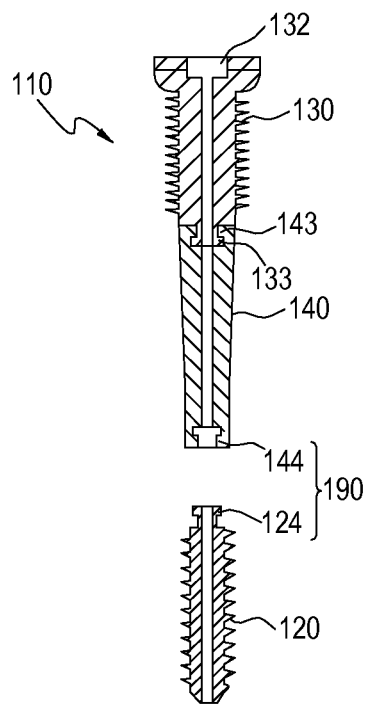
FIG. 7 is a schematic exploded sectional view of a joint structure in a third implementation manner of the present invention.

Referring to FIG. 7, it shows a joint structure 190 according to a third implementation manner of the present invention. In an injection molding manner of the joint structure 190, the front portion 120 includes a first wrapped portion 124, and a leading end of the shaft portion 140 includes a first wrapping portion 144, that is, the first wrapped portion 124 and the first wrapping portion 144 are formed to the joint structure 190. When the first wrapping portion 144 of the shaft portion 140 wraps the first wrapped portion 124 of the front portion 120, the front portion 120 is joined to the leading end of the shaft portion 140.

Likewise, when a second wrapping portion 143 of the shaft portion 140 wraps a second wrapped portion 133 of the rear portion 130, the rear portion 130 is joined to a trailing end of the shaft portion 140.

Figure 8:
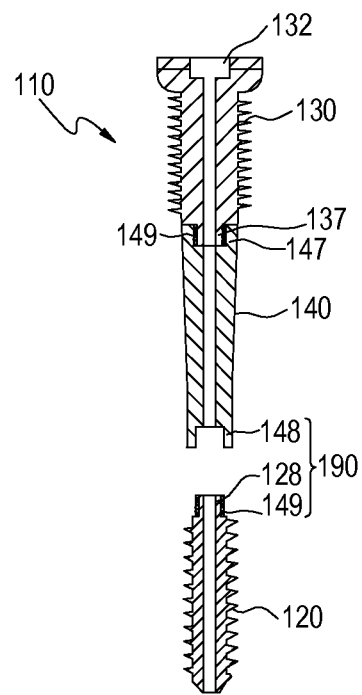
FIG. 8 is a schematic exploded sectional view of a joint structure in a fourth implementation manner of the present invention.

Referring to FIG. 8, it shows a joint structure 190 according to a fourth implementation manner of the present invention. In an adhering manner of the joint structure 190, the front portion 120 includes a first plug 128, and a leading end of the shaft portion 140 includes a first socket 148, that is, the first plug 128, the first socket 148, and adhesive 149 are formed to the joint structure 190. When the first plug 128 of the front portion 120 is adhered to the first socket 148 of the shaft portion 140 by using the adhesive 149, the front portion 120 is joined to the leading end of the shaft portion 140. Likewise, when a second plug 137 of the rear portion 130 is adhered to a second socket 147 of the shaft portion 140 by using the adhesive 149, the rear portion 130 is joined to a trailing end of the shaft portion 140.

Referring to FIG. 3 again, it shows the bone screw 110 according to the first embodiment of the present invention. The bone screw 110 includes a front portion 120, a rear portion 130, and a shaft portion 140 which are all hollow inside and in communication with each other. An outer surface of the front portion 120 is formed with a thread. In this embodiment, an outer surface of the rear portion 130 can also be formed with a thread. In other embodiments, an outer surface of the rear portion 130 can not be formed with a thread. The front portion 120 and the rear portion 130 are made of a biomedical metal material such as titanium, a titanium alloy, vitallium, or stainless steel. Preferably, the front portion 120 and the rear portion 130 are made of the same material.

The shaft portion 140 is located between the front portion 120 and the rear portion 130, and does not have a thread. The shaft portion 140 can be made of a polymer material, for example, a thermoplastic such as poly ether ether kefone (PEEK) or polyethylene (PE).

The Young's Modulus of the shaft portion 140 is smaller than that of the front portion 120 and that of the rear portion 130. For example, the Young's Modulus of PEEK is 3,700 Mpa, the Young's Modulus of PE ranges from 200 Mpa to 1,100 Mpa, and the Young's Modulus of titanium ranges from 105,000 Mpa to 120,000 Mpa. Therefore, it can be seen that the Young's Modulus of PEEK and that of PE are smaller than the Young's Modulus of titanium. The Young's Modulus is also referred to as the Modulus of Elasticity, that is, a slope of an elastic region on a stress-strain curve. The smaller the Young's Modulus is, the more easily the deformation occurs. The greater the Young's Modulus is, the higher the material stiffness is, which means that a greater bond force exists between the atoms and the shape and size are more easily maintained within an elastic load range.

Figure 9:
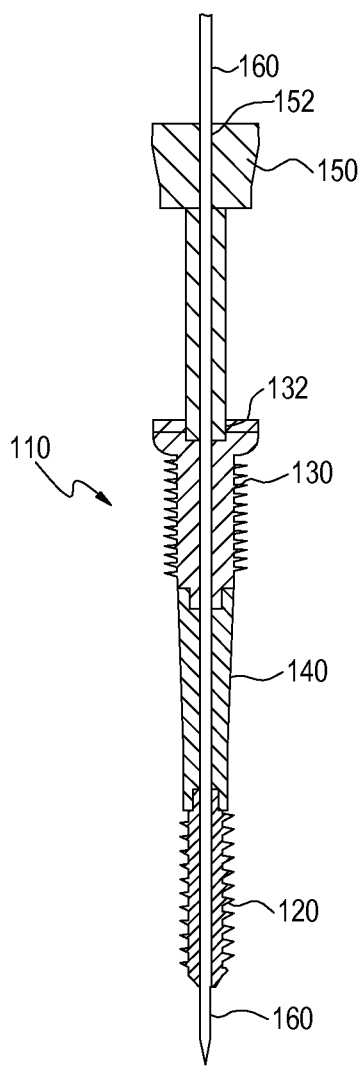
FIG. 9 is a schematic sectional view of a tool for mounting and removing a bone screw according to an embodiment of the present invention.

Referring to FIG. 9, it shows a tool for mounting and removing a bone screw according to an embodiment of the present invention. The mounting and removing tool includes a guide needle 160 and a hollow screw driver 150. The rear portion 130 of the bone screw 110 of the present invention includes a polygonal hole 132 located at a central line of the rear portion 130. The hollow screw driver 150 is adapted to be inserted into the polygonal hole 132 of the bone screw 110, and drives the bone screw 110 to rotate in a clockwise direction or a counterclockwise direction. The hollow screw driver 150 includes a through hole 152 located at a central line of the hollow screw driver 150. The guide needle 160 is adapted to pass through the through hole 152 of the hollow screw driver 150 and the polygonal hole 132 of the bone screw 110, and is exposed from the front portion 120 of the bone screw 110.

Figure 10:
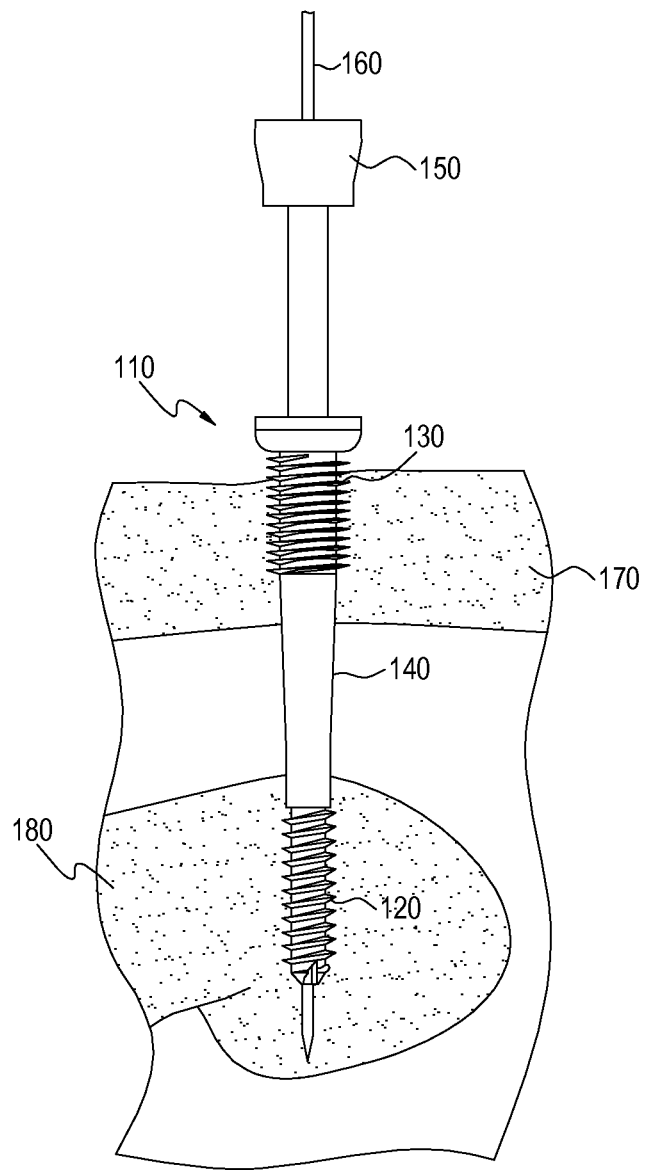
FIG. 10 is a schematic sectional view of a tool for mounting and removing a bone screw according to an embodiment of the present invention, wherein the bone screw is fixed into two bones through pre-punched holes.

Referring to FIG. 10, the bone screw 110 is fixed, by using the guide needle 160 and the hollow screw driver 150, into two bones, for example, a first bone 170 and a second bone 180, through pre-punched holes. In this embodiment, if it is required to treat the dislocation of an acromioclavicular joint, and the first bone 170 and the second bone 180 are respectively a clavicle and a coracoid, the guide needle 160 is first inserted into the coracoid and the clavicle through prepunched holes, the bone screw 110 is then sleeved on the guide needle 160 and guided thereby, and the hollow screw driver 150 is also sleeved on the guide needle 160 and is inserted to the polygonal hole 132 of the bone screw 110, so as to fix the front portion 120 of the bone screw 110 into the coracoid and fix the rear portion 130 into the clavicle, wherein the coracoid is a cancellous bone.

Figure 11:
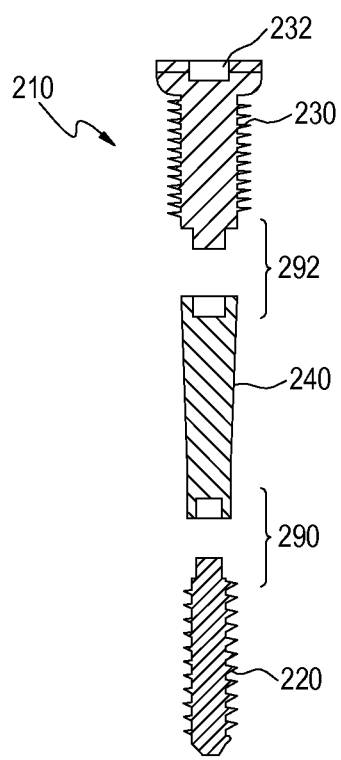
FIG. 11 is a schematic exploded sectional view of a bone screw according to a second embodiment of the present invention.

Referring to FIG. 11, it shows a bone screw 210 according to a second embodiment of the present invention. The bone screw 210 of the second embodiment is substantially similar to the bone screw 110 of the first embodiment, wherein similar elements are marked by similar symbols. Different from the bone screw of the first embodiment, the bone screw 210 of the second embodiment includes a front portion 220, a rear portion 230, and a shaft portion 240 which are all solid. The front portion 220 and the rear portion 230 are fixedly joined to the shaft portion 240 through a joint structure 290 and a joint structure 292 respectively, so as to form an integral bone screw 210. The shaft portion 240 is located between the front portion 220 and the rear portion 230. The Young's Modulus of the shaft portion 240 is smaller than that of the front portion 220 and that of the rear portion 230. The shaft portion 240 can be made of a polymer material, for example, a thermoplastic such as PEEK or PE. The rear portion 230 includes a polygonal hole 232 located at a central line of the rear portion 230. A screw driver (not shown) is inserted into the polygonal hole 232 of the bone screw 210, and drives the bone screw 210 to rotate in a clockwise direction or a counterclockwise direction.

The bone screw of the present invention has a fixing function in the case of a bone fracture or joint dislocation, and mainly has the following advantages. 1. The Young's modulus of the shaft portion is smaller than that of the front portion and that of the rear portion, thereby providing the bone screw with moderate elasticity. 2. After being fixed into two bones of the body, the bone screw can buffer and absorb the receiving force, thereby decreasing the force received by the bones when the front and rear portions are fixed therein, and further lowering the loosening probability of the bone screw. 3. The bone screw is integrally designed, so the wound after a surgery is small; and the bone screw respectively passes through and fixedly unites a first bone and a second bone, so as to reposition and fix the dislocated/fractured portion, thereby simplifying the surgical procedures and shortening the surgery duration.

The present invention provides a bone screw having a shaft portion with moderate elasticity (that is, the Young's Modulus of the shaft portion is smaller than that of the front portion and that of the rear portion). After being implanted into two bones of the body, the bone screw can buffer and absorb the receiving force, thereby decreasing the force received by the cancellous bone, and further lowering the loosening probability of the bone screw. Moreover, by using the bone screw of the present invention, the wound after a surgery is small; and during a surgery, a single bone screw can be positioned and fixed by using an image guided surgical navigation system (C-arm), so as to achieve the efficacy of a minimally invasive surgery, and improve the surgery efficiency and effect, thereby effectively facilitating a bone fracture internal fixation surgery for a clinician, improving the recovery effect and efficiency, lowering the occurrence of a complication, and reducing the waste of medical resources.

To sum up, the implementation manners or embodiments of the technical solutions adopted by the present invention to solve the problems are merely illustrative, and are not intended to limit the scope of the present invention. Any equivalent variation or modification made without departing from the scope or spirit of the present invention shall fall within the appended claims of the present invention.

What is claimed is:

1. A bone screw, comprising:
   a front portion and a rear portion; and
   a shaft portion, fixedly joined to said front portion and said rear portion, so as to form an integral bone screw, wherein the Young's Modulus of the shaft portion is smaller than that of the front portion and that of the rear portion;
   wherein said front portion, said shaft portion and said rear portion being all hollow inside and in communication with each other, said rear portion comprising a polygonal hole located at a central line of said rear portion, whereby a hollow screw driver is adapted to be inserted into the polygonal hole, and a guide needle is adapted to pass through a through hole of the hollow screw driver and the polygonal hole; and
   the shaft portion is made of a polymer material, and the front portion and the rear portion are made of a biomedical metal material.

2. The bone screw according to claim 1, wherein the front portion comprises a first thread, the rear portion comprises a second thread, the shaft portion comprises a first and a second screw hole, and the first and the second thread are screwed into the first and the second screw hole respectively.

3. The bone screw according to claim 1, wherein the front portion comprises a first groove, the rear portion comprises a second groove, the shaft portion comprises a first and a second protrusion, and the first and the second protrusion are snapped into the first and the second groove respectively.

4. The bone screw according to claim 1, wherein the front portion comprises a first wrapped portion, the rear portion comprises a second wrapped portion, the shaft portion comprises a first and a second wrapping portion, and the first and the second wrapping portion are used to wrap the first and the second wrapped portion respectively.

5. The bone screw according to claim 1, wherein the front portion comprises a first plug, the rear portion comprises a second plug, the shaft portion comprises a first and a second socket, and the first and the second plug are inserted into the first and the second socket respectively.

6. The bone screw according to claim 1, wherein the polymer material is poly ether ether kefone (PEEK) or polyethylene (PE), and the biomedical metal material is titanium, a titanium alloy, vitallium, or stainless steel.

7. The bone screw according to claim 1, wherein the front portion is configured to be fixed into a first bone, and the rear portion is configured to be fixed into a second bone.

8. A method for manufacturing a bone screw, comprising the following steps of:
   providing a front portion, a shaft portion, and a rear portion, wherein the Young's Modulus of the shaft portion is smaller than that of the front portion and that of the rear portion; and
   fixedly joining the front portion and the rear portion to the shaft portion in a screwing manner, a snapping manner, an injection molding manner, or an adhering manner, so as to form an integral bone screw;
   wherein said front portion, said shaft portion and said rear portion being all hollow inside and in communication with each other, said rear portion comprising a polygonal hole located at a central line of said rear portion, whereby a hollow screw driver is adapted to be inserted into the polygonal hole, and a guide needle is adapted to pass through a through hole of the hollow screw driver and the polygonal hole; and the shaft portion is made of a polymer material, and the front portion and the rear portion are made of a biomedical metal material.

* * * * *